United States Patent
Zhang

(10) Patent No.: US 8,657,855 B2
(45) Date of Patent: Feb. 25, 2014

(54) SPINAL FIXATION IMPLANT FOR MOUNTING TO SPINOUS PROCESSES AND RELATED METHOD

(75) Inventor: Jeffrey Zhang, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 79 days.

(21) Appl. No.: 13/275,094

(22) Filed: Oct. 17, 2011

(65) Prior Publication Data

US 2013/0096614 A1 Apr. 18, 2013

(51) Int. Cl.
*A61B 17/70* (2006.01)
*A61B 17/88* (2006.01)

(52) U.S. Cl.
USPC .............. 606/248; 606/250; 606/279; 606/70

(58) Field of Classification Search
CPC ........... A61B 17/7029; A61B 17/7043; A61B 17/7049; A61B 17/7062; A61B 17/7067
USPC ............. 606/248–249, 250–253, 263, 70, 71, 606/279
See application file for complete search history.

(56) References Cited

U.S. PATENT DOCUMENTS

| | | | |
|---|---|---|---|
| 4,697,582 A * | 10/1987 | William | 606/254 |
| 5,496,318 A | 3/1996 | Howland et al. | |
| 5,645,599 A | 7/1997 | Samani | |
| 5,725,582 A * | 3/1998 | Bevan et al. | 606/263 |
| 5,947,966 A * | 9/1999 | Drewry et al. | 606/252 |
| 6,190,387 B1 | 2/2001 | Zucherman et al. | |
| 6,296,643 B1 | 10/2001 | Hopf et al. | |
| 6,402,751 B1 | 6/2002 | Hoeck et al. | |
| 7,048,736 B2 | 5/2006 | Robinson et al. | |
| 7,442,208 B2 | 10/2008 | Mathieu et al. | |
| 7,588,592 B2 | 9/2009 | Winslow et al. | |
| 7,641,673 B2 | 1/2010 | Le Couedic et al. | |
| 7,727,233 B2 | 6/2010 | Blackwell et al. | |
| 7,806,911 B2 * | 10/2010 | Peckham | 606/248 |
| 8,287,569 B1 * | 10/2012 | Powell | 606/248 |
| 2002/0138077 A1 * | 9/2002 | Ferree | 606/61 |
| 2005/0010222 A1 * | 1/2005 | Cordaro | 606/61 |
| 2008/0021466 A1 * | 1/2008 | Shadduck et al. | 606/61 |
| 2008/0114455 A1 | 5/2008 | Lange et al. | |
| 2008/0140125 A1 * | 6/2008 | Mitchell et al. | 606/279 |
| 2008/0154307 A1 * | 6/2008 | Colleran et al. | 606/257 |
| 2008/0177326 A1 * | 7/2008 | Thompson | 606/277 |
| 2008/0183211 A1 | 7/2008 | Lamborne et al. | |
| 2008/0183218 A1 | 7/2008 | Mueller et al. | |
| 2008/0281359 A1 * | 11/2008 | Abdou | 606/246 |
| 2008/0281360 A1 | 11/2008 | Vittur et al. | |
| 2009/0198277 A1 | 8/2009 | Gordon et al. | |
| 2009/0264927 A1 | 10/2009 | Ginsberg et al. | |
| 2010/0036419 A1 | 2/2010 | Patel et al. | |
| 2010/0324601 A1 | 12/2010 | Allard et al. | |
| 2011/0144692 A1 | 6/2011 | Saladin et al. | |
| 2011/0152937 A1 | 6/2011 | Trieu | |
| 2011/0166600 A1 | 7/2011 | Lamborne et al. | |
| 2011/0172709 A1 | 7/2011 | Lyons et al. | |
| 2011/0196429 A1 * | 8/2011 | Hua | 606/279 |

* cited by examiner

*Primary Examiner* — Eduardo C. Robert
*Assistant Examiner* — Julianna N Harvey

(57) ABSTRACT

A spinal implant has two pairs of mounting plates or "staples," two rods, and a crosslink. Each mounting plate mounts to a lateral side of a spinous process. Each rod interconnects a pair of mounting plates. The crosslink is disposed through the interspinous space and interconnects the rods. The crosslink hinders movement of the rods away from each other. The rods have a flexural modulus less than the mounting plates. The rod flexibility allows a small amount of relative movement of the vertebrae, which may be helpful in promoting fusion.

20 Claims, 11 Drawing Sheets

SPINAL FIXATION IMPLANT FOR MOUNTING TO SPINOUS PROCESSES AND RELATED METHOD

BACKGROUND

The present invention generally relates to devices and methods for stabilizing vertebral members, and more particularly, to spinal fixation implants that mount onto the spinous processes.

Vertebral members typically comprise a vertebral body, pedicles, laminae, and processes. The processes are projections that serve as connection points for the ligaments and tendons, and typically include the articular processes, transverse processes, and the spinous process. Intervertebral discs are located between adjacent vertebral bodies to permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion. One manner of correcting the damage involves mounting a spinal implant onto the spinous processes, typically in association with a fixation process such as anterior lumbar interbody fusion (ALIF), posterior lumbar interbody fusion (PLIF), intertransverse lumbar interbody fusion (ILIF), and the like. See, for example, the spinal implant sold under the trade name CD HORIZON SPIRE™ by Medtronic Spinal and Biologics of Memphis, Tenn., and the devices described in U.S. Patent Application Publication 2006/0247640 and U.S. Pat. No. 7,048,736. While these devices provide some solutions, they may not be ideal for some situations. As such, there remains a need for alternative spinal implants and related methods.

SUMMARY

In one embodiment, the present application is directed to a spinal implant with two pairs of mounting plates or "staples," two rods, and a crosslink. Each mounting plate mounts to a lateral side of a spinous process. Each rod interconnects a pair of mounting plates. The crosslink is disposed through the interspinous space and interconnects the rods. The crosslink hinders movement of the rods away from each other. The rods have a flexural modulus less than the mounting plates. The rod flexibility allows a small amount of relative movement of the vertebrae, which may be helpful in promoting fusion.

The spinal implant, in one embodiment, comprises first and second mounting plates disposed in spaced relation to each other. The first mounting plate has a first rod-receiving recess therein opening toward the second mounting plate at a first opening. The first mounting plate has a plurality of teeth on a first medial face configured to bite into a spinous process. The second mounting plate has a second rod-receiving recess therein opening toward the first mounting plate at a second opening. The second mounting plate has a plurality of teeth on a second medial face configured to bite into a spinous process. A first rod, distinct from and interconnecting the first and second mounting plates, is disposed in the first and second recesses. The implant also comprises third and fourth mounting plates disposed in spaced relation to each other. The third mounting plate has a third rod-receiving recess therein opening toward the fourth mounting plate at a third opening. The third mounting plate has a plurality of teeth on a third medial face configured to bite into a spinous process. The fourth mounting plate has a fourth rod-receiving recess therein opening toward the third mounting plate at a fourth opening. The fourth mounting plate has a plurality of teeth on a fourth medial face configured to bite into a corresponding spinous process. A second rod, distinct from and interconnecting the third and fourth mounting plates, is disposed in the third and fourth recesses. The first and second rods have respective first and second longitudinal axes spaced from each other. The first and second rods also have respective first and second lateral surfaces hieing directly away from the other rod. The first and third medial faces face generally toward each other, and the second and fourth medial faces face generally toward each other. A link interconnects the first and second rods. The link is disposed between the first and second mounting plates and between the second and fourth mounting plates. The link is further disposed partially laterally outboard of both the first and second rods. The link engages at least one of the first and second lateral faces. The link operative to hinder movement of the first and second rods away from each other. The first and second rods have a flexural modulus that is less than a flexural modulus of the mounting plates.

Some or all of the embodiments may have the following aspects. The first and third medial faces may face directly toward each other. The first recess may have a first abutment flange disposed opposite the first opening and surrounding the first longitudinal axis, the second recess may have a second abutment flange disposed opposite the second opening and surrounding the first longitudinal axis, the first rod abutting the first and second abutment flanges. The link may extend generally perpendicular to the first and second longitudinal axes. The link may comprise a crosslink member having first and second spaced apart cavities, with the first rod clampingly received in the first cavity and the second rod clampingly received in the second cavity. First and second fasteners may extend into the first and second cavities of the crosslink member, respectively, to engage the first and second rods, respectively. Alternatively, the link may comprise a band, optionally an elastic band, that surrounds the first and second longitudinal axis. The first and second rods may comprise PEEK.

In another aspect of the invention, a method of implanting a spinal implant comprises affixing a first mounting plate to a first lateral side of a superior spinous process by having a first plurality of teeth of the first mounting plate bite into the superior spinous process; affixing a second mounting plate to the first lateral side of an inferior spinous process by having a second plurality of teeth of the second mounting plate bite into the inferior spinous process; affixing a third mounting plate to a second lateral side of the superior spinous process by having a third plurality of teeth of the third mounting plate bite into the superior spinous process; and affixing a fourth mounting plate to the second lateral side of the inferior spinous process by having a fourth plurality of teeth of the fourth mounting plate bite into the inferior spinous process. The first mounting plate has a first rod-receiving recess therein opening toward the second mounting plate at a first opening. The second mounting plate has a second rod-receiving recess therein opening toward the first mounting plate at a second opening. The wherein the third mounting plate has a third rod-receiving recess therein opening toward the fourth mounting plate at a third opening. The fourth mounting plate has a fourth rod-receiving recess therein opening toward the third mounting plate at a fourth opening. The first and second mounting plates are interconnected by a first rod that extends through the first and second openings and into the first and second recesses. The third and fourth mounting plates are interconnected by a second rod that extends through the third and fourth openings into the third and fourth recesses. The first and second rods have respective first and second longitudinal axes spaced from each other. The first and second rods have respective first and second lateral surfaces facing directly away from the other rod. The method continues by thereafter inhibiting movement of the first and second rods away from each other by interconnecting the first and second rods with a link, with the link disposed partially outboard of, and engaging, at least one of the first and second lateral faces. The first and second rods have a flexural modulus that is less than a flexural modulus of the mounting plates.

Some or all of the embodiments may have the following aspects. The link may comprise a band, optionally an elastic band, with the interconnecting the first and second rods comprising surrounding the first and second longitudinal axes with the band. The link may comprise a crosslink member having first and second spaced apart cavities, with the interconnecting the first and second rods comprises clamping the first rod in the first cavity and clamping the second rod in the second cavity. The clamping the first rod may comprise tightening a first fastener that extends into the first cavity to engage the first rod. The clamping the second rod may comprise tightening a second fastener that extends into the second cavity to engage the second rod. The first rod may be disposed in the first and second openings of the first and second mounting plates, respectively, prior to the affixing of the first and second mounting plates to the superior and inferior spinous processes, respectively. The second rod may be disposed in the third and fourth openings of the third and fourth mounting plates, respectively, prior to the affixing of the third and fourth mounting plates to the superior and inferior spinous processes, respectively. The first mounting plate may be affixed to the superior spinous process prior to the affixing the second mounting plate to the inferior spinous process, and/or the third mounting plate may be affixed to the superior spinous process prior to the affixing the fourth mounting plate to the inferior spinous process.

Of course, the present invention is not limited to the above features and advantages. Indeed, those skilled in the art will recognize additional features and advantages upon reading the following detailed description, and upon viewing the accompanying drawings.

DETAILED DESCRIPTION

In one embodiment, the present application is directed to a spinal implant with two pairs of mounting plates or "staples," two rods, and a crosslink. Each mounting plate mounts to a lateral side of a spinous process. Each rod interconnects a pair of mounting plates. The crosslink is disposed through the interspinous space and interconnects the rods. The crosslink hinders movement of the rods away from each other. The rods have a flexural modulus less than the mounting plates. The rod flexibility allows a small amount of relative movement of the vertebrae, which may be helpful in promoting fusion.

Figure 1:
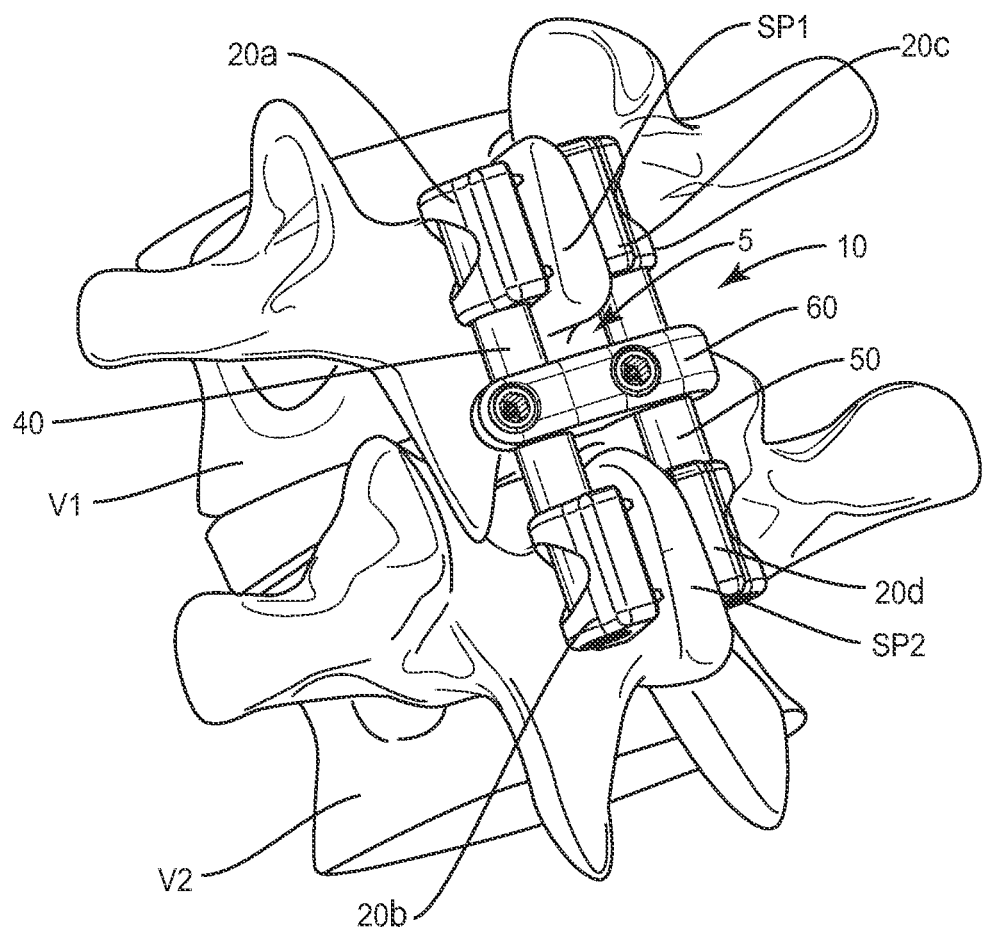
FIG. 1 shows a spinal implant according to one embodiment mounted to a spinal column.
Figure 2:
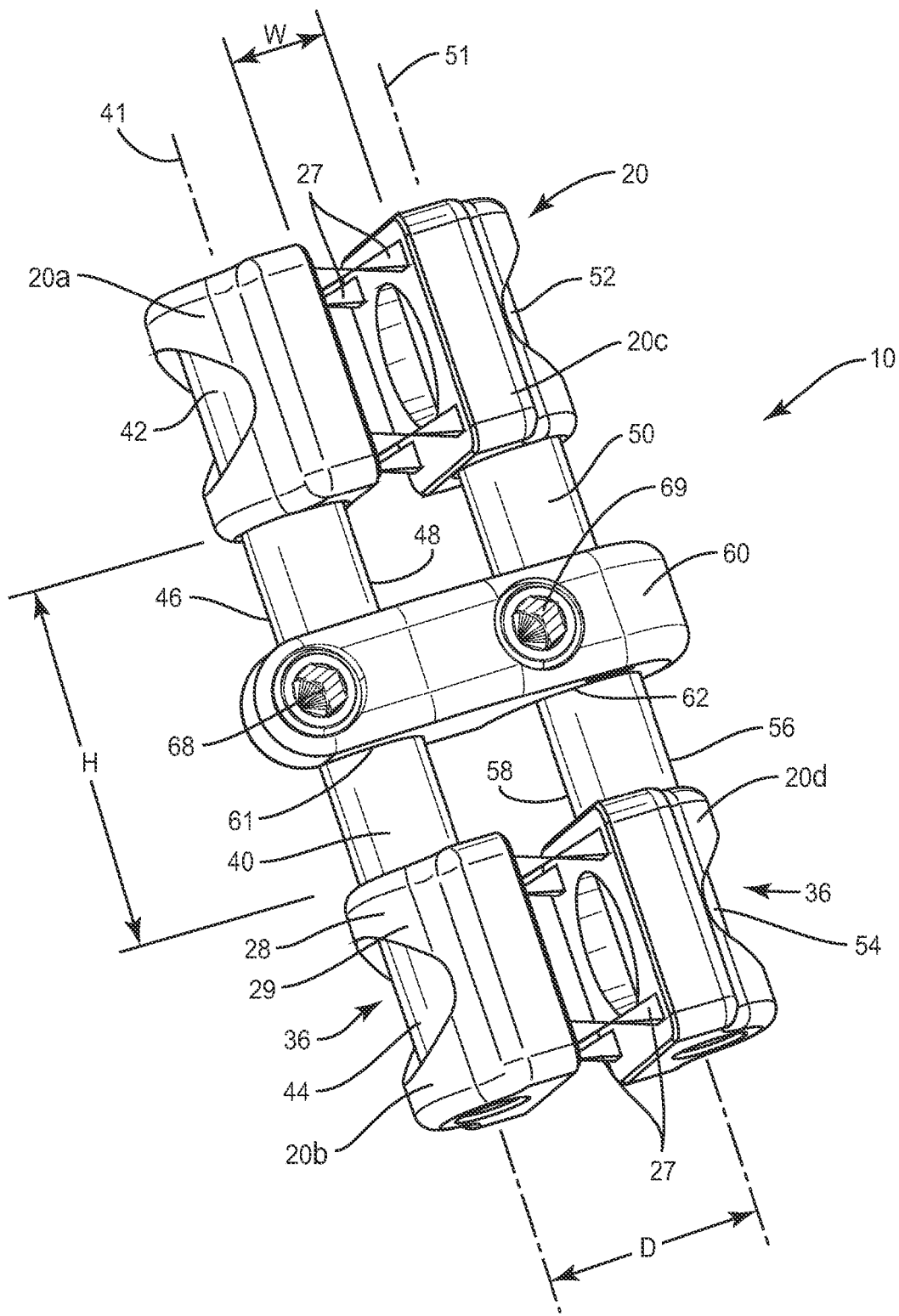
FIG. 2 shows a perspective view of the spinal implant of FIG. 1.
Figure 3:
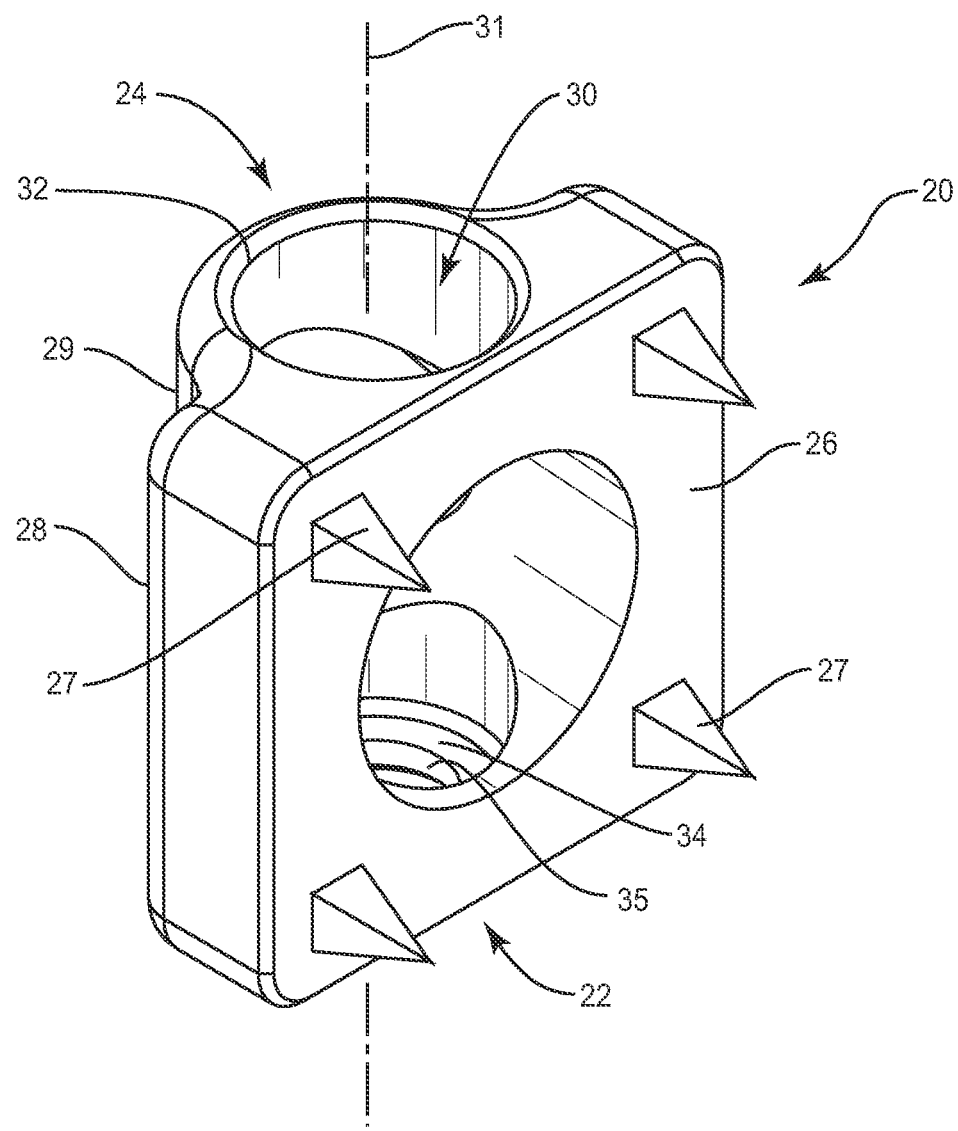
FIG. 3 shows a perspective view of a mounting plate of the implant of FIG. 2.
Figure 4:
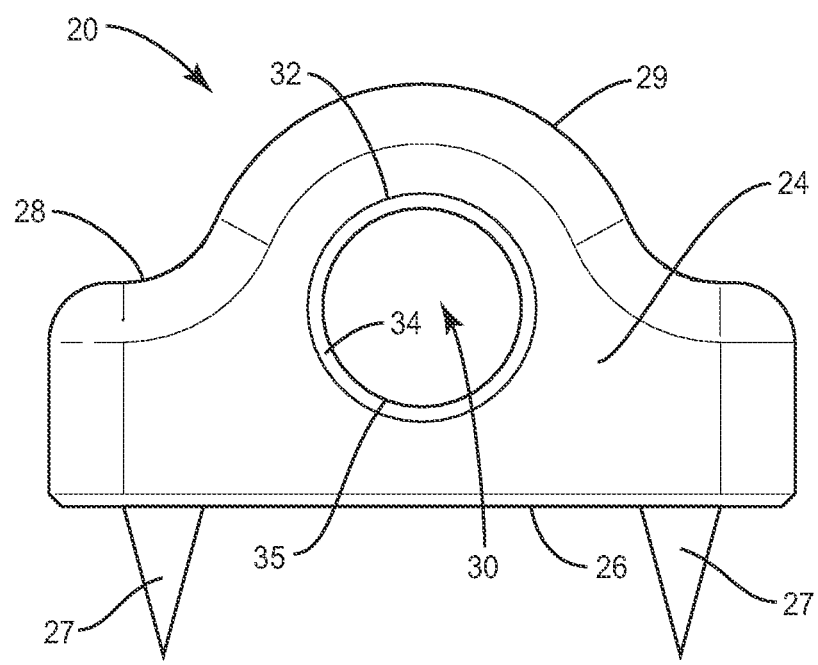
FIG. 4 shows an end view of the mounting plate of FIG. 2.
Figure 5:
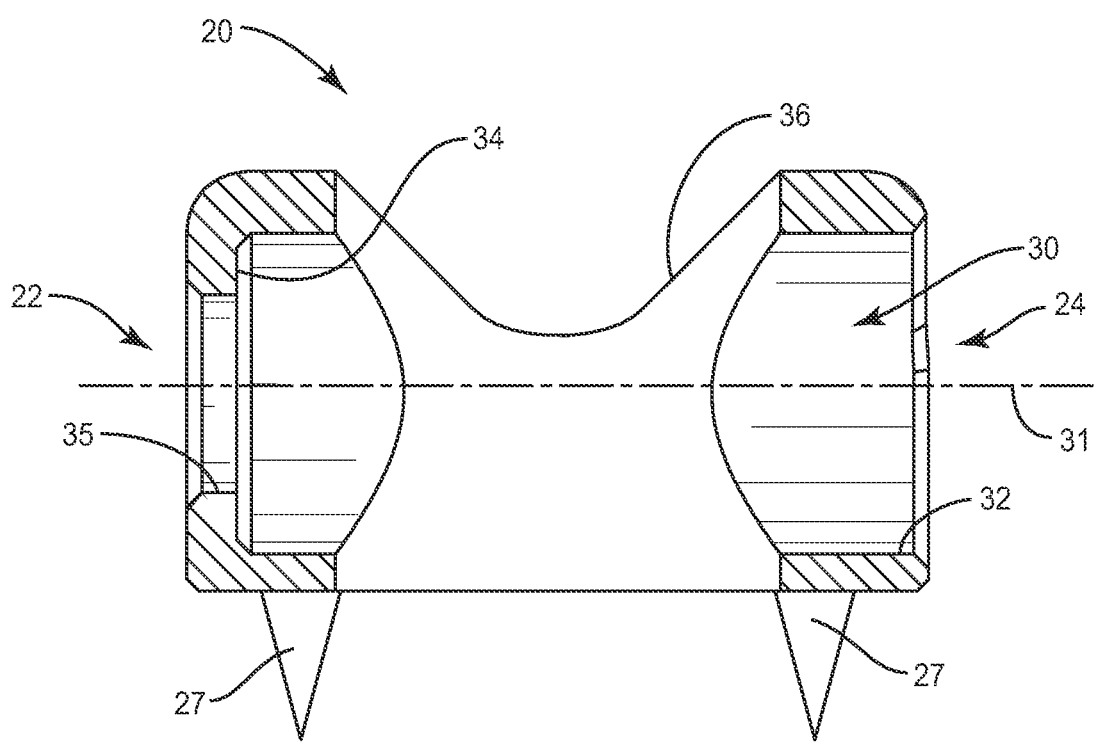
FIG. 5 shows a cross-sectional view of the mounting plate of FIG. 2.
Figure 6:
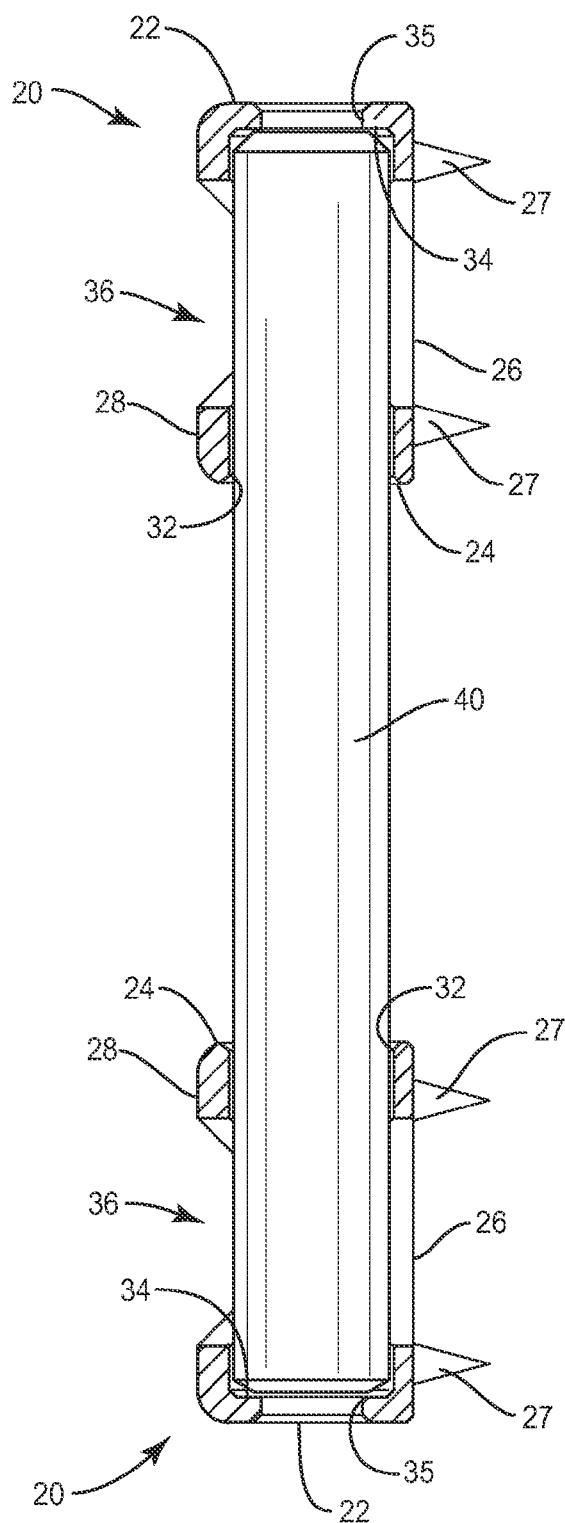
FIG. 6 shows a cross-sectional view of two mounting plates and an associated rod.

Referring to FIG. 1, a spinal implant according to one embodiment and generally designated 10 is shown clampingly mounted to the spinous process SP1 of a superior vertebra V1 and a spinous process SP2 of an inferior vertebra V2. A portion of the implant 10, in particular crosslink 60, extends transversely through the interspinous space 5 between the two spinous processes SP1, SP2. The implant, shown more clearly in FIG. 2, includes four mounting plates 20 (20a, 20b, 20c, 20d) arranged in two pairs, two rods 40,50 each interconnecting two mounting plates 20, and a crosslink 60 which laterally interconnects the rods 40,50.

The mounting plates 20 are advantageously identical, albeit mounted in different orientations. As such, mounting plate 20a will be described and referred to as mounting plate 20; it being understood that the other mounting plates 20b, 20c, 20d are similar. Mounting plate 20 has an outer end 22, an inner end 24, a medial face 26, and a lateral face 28. The outer end 22 is intended to be disposed facing away from the other mounting plate 20 that shares the common rod 40, while inner end 24 is intended to be disposed facing toward the other mounting plate 20. Medial face 26 is intended to face toward a lateral side of a spinous process (e.g., SP1) and includes a plurality of teeth 27 that are configured for biting into the corresponding spinous process. The medial face 26 may advantageously be generally planar (excluding the teeth 27), although such is not required, and medial face 26 may be contoured (e.g., curvate or stepped) if desired. The lateral face 28 faces generally opposite the medial face 26, and includes a contoured boss 29. Rod-receiving cavity 30 extends from inner end 24 at opening 32 into boss 29 along cavity axis 31. Opening 32 is sized and configured to receive the corresponding rod 40. Cavity 30 conceptually terminates at abutment flange 34 disposed proximate outer end 22. If desired, a secondary opening 35 may extend from cavity 30 to outer end 22. As can be appreciated, secondary opening 35 is smaller than opening 32, such that rod 40 cannot pass therethrough. Mounting plate 20 may also include, if desired, a view port 36 that extends from the medial face 26 to the lateral face 28 through cavity 30. Mounting plate 20 is formed of a suitable rigid material, such as titanium and its alloys, cobalt-chrome, stainless steel, and other metallic materials.

Rod 40 is elongate along rod longitudinal axis 41 from a superior end 42 to an inferior end 44. Rod 40 advantageously has a generally cylindrical shape with a circular cross-section, although other cross-sectional shapes, such as hexagonal, star, oval, and the like may alternatively employed. Further, while the rod 40 need not be uniform in cross section along its length, such is believed to be advantageous. Rod 40 has a medial face 48 facing the opposing rod 50, and a lateral face 46 facing directly away from the other rod 50. The rod 40 may be formed of a suitable polymer material such as polyetheretherketone (PEEK) (fiber reinforced or not) and the like, a suitable low modulus metallic material such as titanium alloys (advantageously with a modulus of elasticity of 50-60 GPa) and the like, alloys of either, or other biocompatible materials known in the art. Rod 40 is advantageously formed of a more flexible material than the mounting plates 20, thus, the flexural modulus of the rod 40 is advantageously less than the flexural modulus of the mounting plates 20.

Rod 50 is advantageously identical to rod 40. Thus, rod 50 is elongate along rod longitudinal axis 51 from a superior end 52 to an inferior end 54. Rod 50 advantageously has a generally cylindrical shape with a circular cross-section, although other cross-sectional shapes, such as hexagonal, star, oval, and the like may alternatively employed. Further, while the rod 50 need not be uniform in cross section along its length, such is believed to be advantageous. Rod 50 has a medial face 58 facing the opposing rod 40, and a lateral face 56 facing directly away from the other rod 40. The rod 50 may be formed of a suitable materials described above with respect to rod 40. Rod 50 is advantageously formed of a more flexible material than the mounting plates 20, thus, the flexural modulus of the rod 50 is advantageously less than the flexural modulus of the mounting plates 20.

Figure 7:
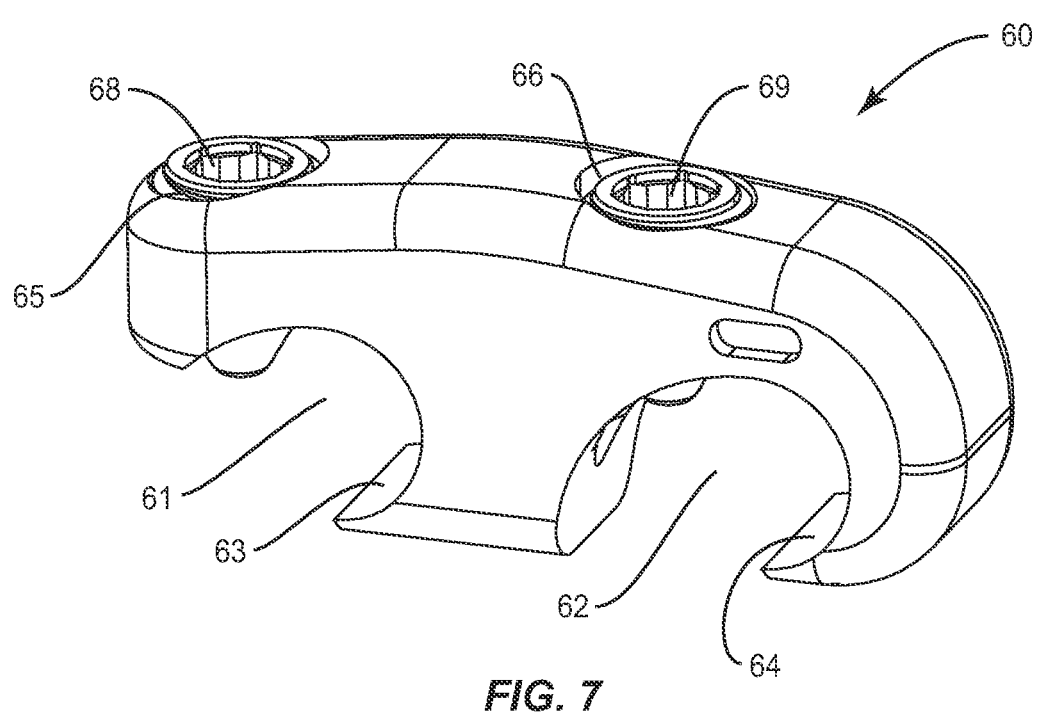
FIG. 7 shows a perspective view of a link of the implant of FIG. 2.
Figure 8:
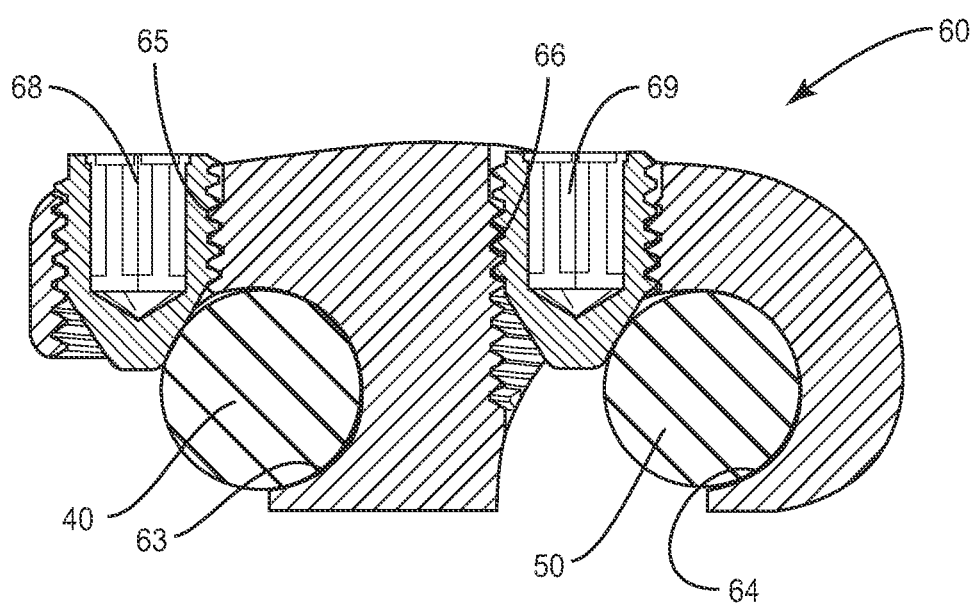
FIG. 8 shows a cross-sectional view of the link of FIG. 7, with rods.

Crosslink 60 interconnects rods 40,50 and is intended to extend through the interspinous space 5, advantageously generally normal to the sagittal plane defined by the spinous processes SP1,SP2. The crosslink 60 is mounted to the rods 40,50 in a transverse orientation in a gap between the mounting plates 20. The longitudinal axis of crosslink 60 is advantageously oriented generally perpendicular to the rod axes 41,51. The crosslink 60 includes two spaced apart cavities 61,62. The cavities 61,62 are sized and configured to receive a corresponding rod 40,50, and therefore have a generally round shape in FIGS. 7-8. Each cavity 61,62 has a respective clamping surface 63, 64 and an associated threaded bore 65, 66. The bores 63,64 are sized and configured to receive corresponding fasteners (e.g., tapered nose setscrews) 68,69. Advancement of the fasteners 68,69 acts to clamp the corresponding rod 40,50 between the fastener 68,69 and the corresponding clamping surface 63,64. Like mounting plates 20, crosslink 60 is formed of a suitable rigid material, such as titanium and its alloys, cobalt-chrome, stainless steel, and other metallic materials.

Figure 9:
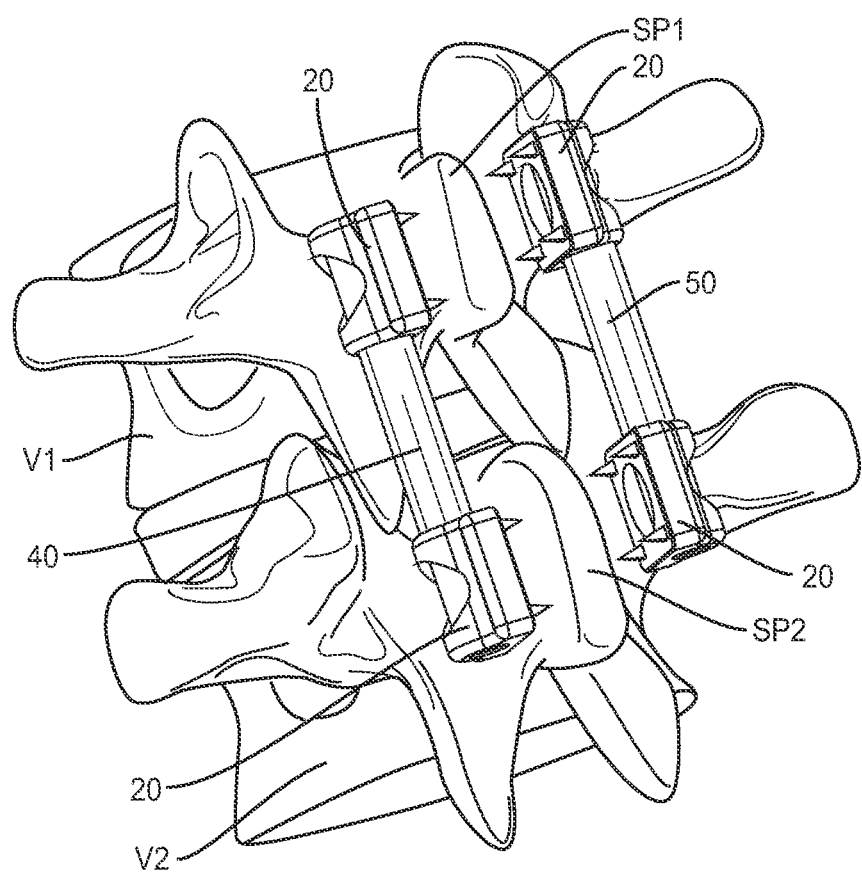
FIG. 9 shows the implant of FIG. 2 during an implantation procedure, prior to affixing the mounting plates to the spinous processes.
Figure 10:
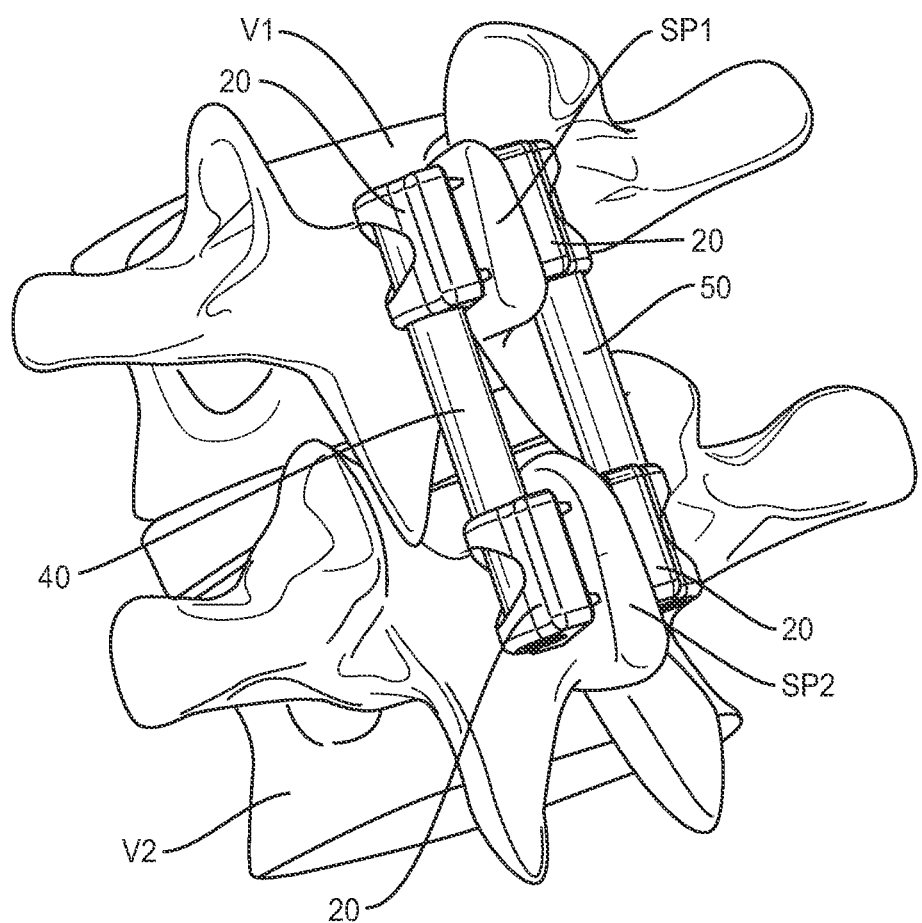
FIG. 10 shows the implant of FIG. 2 during the implantation procedure of FIG. 9, after affixing the mounting plates to the spinous processes and prior to addition of the link.

Implant 20 may be installed in a variety of ways. For example, mounting plates 20a, 20b may be joined with rod 40 by sliding rod 40 through openings 32 and into cavities 30. Advantageously, the rod 40 is fully seated into cavities 30 such that it rests against abutment flanges 34. Thus, mounting plates 20a,20b associated with rod 40 are positioned a distance H apart. This assembly is then placed along a lateral side of spinous processes SP1,SP2. For purposes of illustration, it will be assumed that the assembly is positioned on the left side of spinous processes SP1,SP2. Note that in positioning the assembly, mounting plate 20a should be adjacent spinous process SP1 with its medial face 26 facing the left lateral side of spinous process SP1 and mounting plate 20b should be adjacent spinous process SP2 with its medial face 26 facing the left lateral side of spinous process SP2. Similarly, mounting plates 20c,20d are joined with rod 50 by sliding rod 50 through openings 32 into cavities 30 of mounting plates 20c, 20d. Rod 50 is advantageously fully seated into cavities 30 such that it rests against abutment flanges 34; thus, mounting plates 20c,20d associated with rod 50 are positioned distance H apart. This assembly is then placed along the right lateral side of spinous processes SP1,SP2 such that mounting plate 20c is adjacent spinous process SP1 with its medial face 26 facing the right lateral side of spinous process SP1 and mounting plate 20d is adjacent spinous process SP2 with its medial face 26 facing the right lateral side of spinous process SP2. See FIG. 9. The mounting plates 20 may then be affixed to the corresponding spinous processes SP1,SP2 by using a suitable tool to force the mounting blocks 20 toward their corresponding spinous processes SP1,SP2 (reducing the distance W between corresponding mounting plates 20 on opposing sides of a spinous process) to have the teeth 27 bite into the spinous processes SP1,SP2. See FIG. 10. The crosslink is then added by inserting rods 40,50 into cavities 61,62 respectively, and tightening fasteners 68,69 to clamp rods 40,50 against clamping surfaces 66. This has the effect of fixing the distance between rod axes 41,51 as distance D. Note that crosslink 60 may or may not apply a compressive force to the rods 40,50 that urges them toward each other.

The crosslink 60, being relatively rigid, helps prevent lateral separation of the rods 40,50. The relatively fixed spacing of the rods 40,50, in turn, helps prevent lateral displacement of the mounting plates 20, thereby helping to keep the teeth 27 firmly anchored to the spinous processes SP1,SP2. Further, the more flexible nature of the rods allows a small relative movement between vertebrae V1,V2 which may be helpful in promoting fusion if the implant is used in conjunction with an interbody fusion implant (disposed in the disc space between the vertebrae V1,V2).

The discussion above has assumed that mounting plates 20a,20b and rod 40 are positioned prior to positioning mounting plates 20c,20d and rod 50; however, this sequence may be reversed. Likewise the left and right dispositions of the mounting plates 20 and rods, 40,50 may be reversed. The discussion has also assumed that the mounting plates 20 are mated to their corresponding rod 40,50 prior to clamping any of the mounting plates 20 to a spinous process SP1,SP2; however, such is not necessary. In some embodiments, mounting plates 20a,20c (or 20b,20d) may be affixed to the corresponding spinous process SR1 or SP2 prior to inserting the rods 40,50 into the cavities, with the other mounting plates 20b,20d (or 20a,20c) subsequently affixed to their spinous process. Note further that the mounting plates 20 may be affixed to their respective spinous processes SP1,SP2 in any suitable sequence; thus, mounting plate 20a may be affixed prior to, or after, or simultaneously with affixing mounting plate 20b, which may in turn occur prior to, after, or simultaneous with affixing mounting plate 20c and/or mounting plate 20d.

Figure 11:
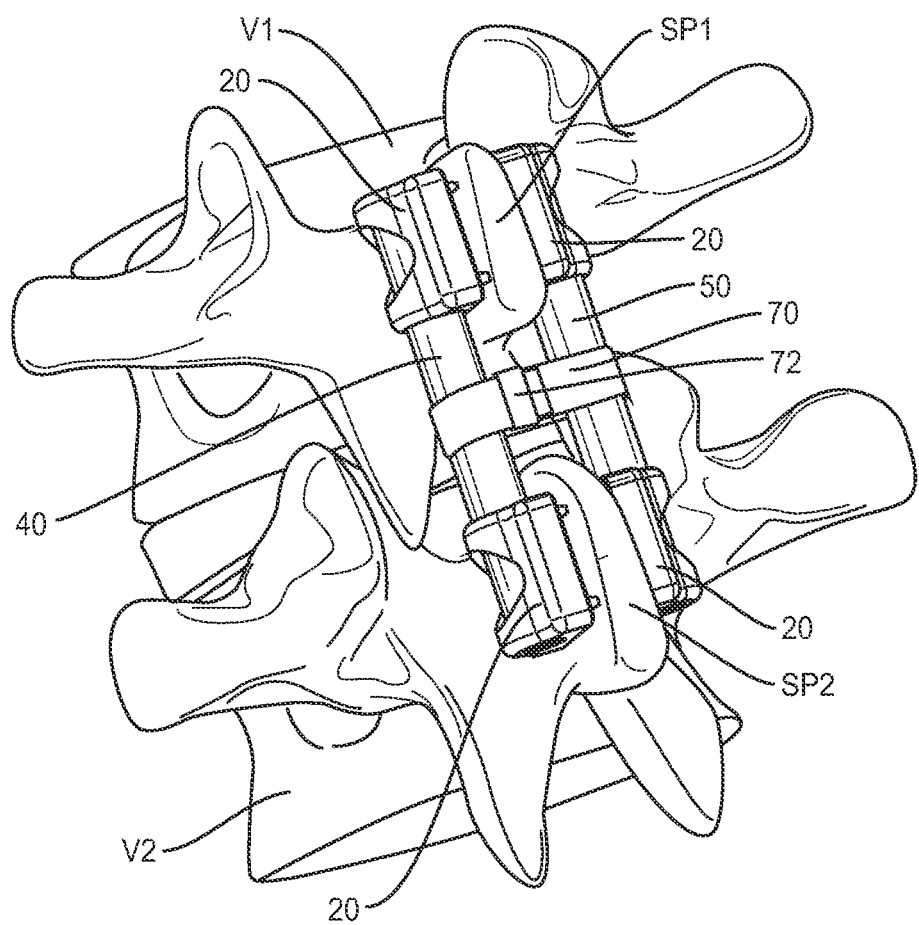
FIG. 11 shows another embodiment of the spinal implant that uses a band to laterally interconnect the rods.

The discussion above has assumed that the rods 40,50 are laterally connected by a rigid bar-like crosslink 60. However, as shown in FIG. 11 the implant in some embodiments may have the rods 40,50 laterally interconnected by a band 70 rather than the crosslink 60 of FIG. 2. This band 70 may be a continuous loop of elastic material, or may have one end secured by a suitable chinch (e.g., crimp connector, suture, etc.). In some embodiments, the band 70 may be suture, wire. In some embodiments, there may be multiple crosslinks 60, bands 70, or a mix thereof.

In the illustrated embodiments, the crosslink member 60 (or band 70) is disposed perpendicular to the rod axes 41,51. However, such is not required, and the crosslink member 60 (or band 70) may be disposed at any suitable angle, such as slight angles to perpendicular (e.g., approximately ±5° from perpendicular), which should be considered as "generally perpendicular" herein.

The discussion above has generally been in the context of the implant 10 being used in the lumbar region of the spine. For example, FIG. 1 shows the implant 10 applied to vertebra L-2 and L-3. However, the implant 10 can be implanted on spinous processes at other levels, including at the lumbar-sacral level. Further, the illustrations have assumed that the medial faces 26 of the various mounting plates 20 are disposed in parallel. However, the medial faces need not be parallel. Any of the mounting plates may be turned to face more anteriorly (or posteriorly) so as to better grip the corresponding spinous process (or sacrum).

The implant 10 may be used during surgical procedures on living patients. The implant may also be used in a nonliving situation, such as within a cadaver, model, and the like. The non-living situation may be for one or more of testing, training, and demonstration purposes.

All U.S. patents, patent application publications, and applications mentioned above are hereby incorporated herein by reference in their entirety.

The present invention may, of course, be carried out in other ways than those specifically set forth herein without departing from essential characteristics of the invention. The present embodiments are to be considered in all respects as illustrative and not restrictive, and all changes coming within the meaning and equivalency range of the appended claims are intended to be embraced therein.

What is claimed is:

1. A spinal implant for connecting adjacent spinous processes, comprising:
    first and second mounting plates disposed in spaced relation to each other; the first mounting plate having a first rod-receiving recess therein opening toward the second mounting plate at a first opening and opening opposite the second mounting plate at a secondary opening that is smaller than the first opening; the first mounting plate having a plurality of teeth on a first medial face configured to bite into a spinous process;
    the second mounting plate having a second rod-receiving recess therein opening toward the first mounting plate at a second opening; the second mounting plate having a plurality of teeth on a second medial face configured to bite into a spinous process;
    a first rod distinct from and interconnecting the first and second mounting plates and disposed in the first and second recesses, the first rod having a uniform diameter that is greater than a maximum width of the secondary opening such that the first rod is prevented from passing through the secondary opening;
    third and fourth mounting plates disposed in spaced relation to each other;
    the third mounting plate having a third rod-receiving recess therein opening toward the fourth mounting plate at a third opening; the third mounting plate having a plurality of teeth on a third medial face configured to bite into a spinous process;
    the fourth mounting plate having a fourth rod-receiving recess therein opening toward the third mounting plate at a fourth opening; the fourth mounting plate having a plurality of teeth on a fourth medial face configured to bite into a corresponding spinous process;
    a second rod distinct from and interconnecting the third and fourth mounting plates and disposed in the third and fourth recesses; the first and second rods having respective first and second longitudinal axes spaced from each other; the first and second rods having respective first and second lateral surfaces facing directly away from the other rod; the first and third medial faces facing generally toward each other;
    the second and fourth medial faces facing generally toward each other;
    a link interconnecting the first and second rods; the link disposed between the first and second mounting plates and between the third and fourth mounting plates;
    the link disposed partially laterally outboard of both the first and second rods; the link engaging at least one of the first and second lateral faces;
    the link operative to hinder movement of the first and second rods away from each other;
    wherein the first and second rods have a flexural modulus that is less than a flexural modulus of the mounting plates, and
    wherein at least one of the plates comprises an aperture extending through a respective medial face such that the aperture is in communication with a respective recess.

2. The spinal implant of claim 1 wherein the first and third medial faces face directly toward each other.

3. The spinal implant of claim 1 wherein the first recess has a first abutment flange disposed opposite the first opening and surrounding the first longitudinal axis; wherein the second recess has a second abutment flange disposed opposite the second opening and surrounding the first longitudinal axis; wherein the first rod abuts the first and second abutment flanges.

4. The spinal implant of claim 1 wherein the link extends generally perpendicular to the first and second longitudinal axes.

5. The spinal implant of claim 1 wherein the link comprises a crosslink member having first and second spaced apart cavities; wherein the first rod is clampingly received in the first cavity and the second rod is clampingly received in the second cavity.

6. The spinal implant of claim 5 further comprising first and second fasteners extending into the first and second cavities of the crosslink member, respectively, and engaging the first and second rods, respectively.

7. The spinal implant of claim 1 wherein the link comprises a band that surrounds the first and second longitudinal axis.

8. The spinal implant of claim 1 wherein the link comprises an elastic band.

9. The spinal implant of claim 1 wherein the first and second rods comprise PEEK.

10. The spinal implant of claim 1 wherein the link comprises a first aperture positioned between the rods and a second aperture that is not positioned between the rods, the apertures each including a fastener disposed therein to fix the rods relative to one another.

11. The spinal implant of claim 10 wherein the apertures extend perpendicular to axes defined by the rods.

12. The spinal implant of claim 1 wherein at least one of the plates is monolithic and comprises a view port extending into a lateral face opposite a respective medial face, the view port being configured to provide visualization of a respective rod disposed within a respective rod-receiving recess.

13. A method of implanting a spinal implant, comprising:
    affixing a first mounting plate to a first lateral side of a superior spinous process by having a first plurality of teeth extending from a medial face of the first mounting plate bite into the superior spinous process;
    affixing a second mounting plate to the first lateral side of an inferior spinous process by having a second plurality of teeth extending from a medial face of the second mounting plate bite into the inferior spinous process;
    affixing a third mounting plate to a second lateral side of the superior spinous process by having a third plurality of teeth extending from a medial face of the third mounting plate bite into the superior spinous process;
    affixing a fourth mounting plate to the second lateral side of the inferior spinous process by having a fourth plurality of teeth extending from a medial face of the fourth mounting plate bite into the inferior spinous process;

wherein the first mounting plate has a first rod-receiving recess therein opening toward the second mounting plate at a first opening and opening opposite the second mounting plate at a secondary opening that is smaller than the first opening;

wherein the second mounting plate has a second rod-receiving recess therein opening toward the first mounting plate at a second opening;

wherein the third mounting plate has a third rod-receiving recess therein opening toward the fourth mounting plate at a third opening;

wherein the fourth mounting plate has a fourth rod-receiving recess therein opening toward the third mounting plate at a fourth opening;

wherein the first and second mounting plates are interconnected by a first rod that extends through the first and second openings and into the first and second recesses, the first rod having a uniform diameter that is greater than a maximum width of the secondary opening such that the first rod is prevented from passing through the secondary opening;

wherein the third and fourth mounting plates are interconnected by a second rod that extends through the third and fourth openings into the third and fourth recesses;

the first and second rods having respective first and second longitudinal axes spaced from each other; the first and second rods having respective first and second lateral surfaces facing directly away from the other rod;

thereafter, inhibiting movement of the first and second rods away from each other by interconnecting the first and second rods with a link, with the link disposed partially outboard of, and engaging, at least one of the first and second lateral faces;

wherein the first and second rods have a flexural modulus that is less than a flexural modulus of the mounting plates, and wherein at least one of the plates comprises an aperture extending through a respective medial face such that the aperture is in communication with a respective recess.

14. The method of claim 13 wherein the link comprises a band; wherein the interconnecting the first and second rods comprises surrounding the first and second longitudinal axes with the band.

15. The method of claim 13 wherein the link comprises an elastic band.

16. The method of claim 13 wherein the link comprises a crosslink member having first and second spaced apart cavities; wherein the interconnecting the first and second rods comprises clamping the first rod in the first cavity and clamping the second rod in the second cavity.

17. The method of claim 16 wherein clamping the first rod comprises tightening a first fastener that extends into the first cavity to engage the first rod; wherein clamping the second rod comprises tightening a second fastener that extends into the second cavity to engage the second rod.

18. The method of claim 13 further comprising disposing the first rod in the first and second openings of the first and second mounting plates, respectively, prior to the affixing of the first and second mounting plates to the superior and inferior spinous processes, respectively.

19. The method of claim 18 further comprising disposing the second rod in the third and fourth openings of the third and fourth mounting plates, respectively, prior to the affixing of the third and fourth mounting plates to the superior and inferior spinous processes, respectively.

20. The method of claim 13 wherein the affixing the first mounting plate to the superior spinous process occurs prior to the affixing the second mounting plate to the inferior spinous process.

* * * * *